(12) United States Patent
Amalric et al.

(10) Patent No.: US 7,226,580 B2
(45) Date of Patent: *Jun. 5, 2007

(54) TOPICAL COMPOSITIONS WITH AN OILY OUTER PHASE AND PROCESS FOR THEIR PREPARATION

(75) Inventors: Chantal Amalric, Blan (FR); Alicia Roso, Saix (FR); Nelly Michel, Maisons Alfort (FR); Guy Tabacchi, Paris (FR)

(73) Assignee: SEPPIC, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/635,898

(22) Filed: Aug. 7, 2003

(65) Prior Publication Data

US 2004/0071642 A1    Apr. 15, 2004

Related U.S. Application Data

(63) Continuation-in-part of application No. 10/220,296, filed as application No. PCT/FR02/00430 on Feb. 5, 2002.

(51) Int. Cl.
*A61K 8/00* (2006.01)
*A61K 8/18* (2006.01)
*A61K 8/02* (2006.01)
*A61K 9/00* (2006.01)

(52) U.S. Cl. .......... 424/59; 424/400; 424/401; 514/844; 514/937; 516/22

(58) Field of Classification Search ........... 424/400, 424/401, 59; 516/22; 514/844, 937
See application file for complete search history.

(56) References Cited

U.S. PATENT DOCUMENTS

| 5,304,334 | A | * | 4/1994 | Lahanas et al. | 516/23 |
| 5,332,595 | A | * | 7/1994 | Gaonkar | 426/602 |
| 5,798,108 | A | * | 8/1998 | Nadaud et al. | 424/401 |
| 5,840,943 | A | * | 11/1998 | Ansmann et al. | 554/166 |
| 5,866,148 | A | | 2/1999 | Hansenne et al. | |
| 6,488,946 | B1 | * | 12/2002 | Milius et al. | 424/401 |

FOREIGN PATENT DOCUMENTS

| JP | 3178917 | | 2/1991 |
| WO | 96/04894 | | 2/1996 |
| WO | WO 00/56438 A1 | * | 9/2000 |
| WO | 02/062305 | | 8/2002 |

* cited by examiner

*Primary Examiner*—Sreeni Padmanabhan
*Assistant Examiner*—Marina Lamm
(74) *Attorney, Agent, or Firm*—Dennison, Schultz & MacDonald

(57) ABSTRACT

A topical composition containing one oily outer phase and two aqueous inner phases, one of which is a gel and a process for its preparation. In a preferred embodiment, the topical composition is a sunscreen emulsion containing one or more sunscreen filter substances.

19 Claims, No Drawings

TOPICAL COMPOSITIONS WITH AN OILY OUTER PHASE AND PROCESS FOR THEIR PREPARATION

This application is a continuation-in-part of U.S. application Ser. No. 10/220,296 filed Sep. 12, 2002, which is a filing under 35 USC 371 of PCT/FR02/00430 filed Feb. 5, 2002.

BACKGROUND OF THE INVENTION

The present invention relates to a novel topical composition consisting of one oily outer phase and two aqueous inner phases, and to a process for the preparation of said composition.

The invention is applicable especially in the cosmetic, pharmaceutical or veterinary field or in the detergent field.

The final texture of traditional emulsions with an oily outer phase is unpleasant for the consumer, having a greasy feel, being difficult to spread and having a sticky effect.

SUMMARY OF THE INVENTION

It has now been discovered that the addition of an emulsion of the "water-in-oil" type to an aqueous gel (or vice-versa) affords an emulsion with an oily outer phase, whereas those skilled in the art would have expected to obtain an emulsion of the "water-in-oil-in-water" type or a phase separation; it is this discovery which forms the basis of the invention. Such an emulsion with an oily outer phase has a fresh, pleasant and non-sticky texture.

Thus, according to a first feature, the invention relates to a topical composition consisting of one oily outer phase and two aqueous inner phases, one of which is a gel.

Advantageously, the oil of the oily outer phase represents at least 2% by weight, preferably from 5 to 20% by weight and generally at most 50% by weight of the topical composition.

According to a second feature, the present invention relates to a process for the preparation of the composition described above, said process comprising the mixing of a "water-in-oil" emulsion (which will hereafter be called a "primary emulsion with an oily outer phase") and an aqueous gel.

Advantageously, said mixture comprises 5 to 80% by weight, preferably 10 to 60% by weight, of the primary emulsion with an oily outer phase and 20 to 95% by weight, preferably 40 to 90% by weight, of aqueous gel.

In the process of the invention, it is of little importance whether the primary emulsion with an oily outer phase is introduced into the aqueous gel or whether the aqueous gel is introduced into the primary emulsion with an oily outer phase. Nevertheless, it can be advantageous to add the primary emulsion with an oily outer phase to the aqueous gel, preferably with slow stirring.

DETAILED DESCRIPTION OF THE INVENTION

The primary emulsion with an oily outer phase generally comprises from 5 to 90% by weight of oil, and preferably from 2 to 50%.

This oil can be selected from one or more of the following oils:

oils of vegetable origin such as sweet-almond oil, coprah oil, monoi oil, castor oil, jojoba oil, olive oil, colza oil, groundnut oil, sunflower oil, wheat germ oil, maize oil, soybean oil, cottonseed oil, alfalfa oil, poppy oil, pumpkin oil, evening primrose oil, millet oil, barley oil, rye oil, safflower oil, candlenut oil, passion flower oil, hazelnut oil, palm oil, shea butter, apricot kernel oil, calophyllum oil, sysymbrium oil, avocado oil and calendula oil;

modified vegetable oils such as the products known under the names Apricot Kernel Oil PEG-6 esters, Olive Oil PEG-6 esters and LABRAFIL®;

oils of animal origin such as squalene and squalane;

mineral oils such as paraffin oil or liquid petrolatum and the mineral oils derived especially from petroleum cuts, such as isoparaffins, having a boiling point of between 300 and 400° C.; and synthetic oils, especially fatty acid esters such as isodecyl neopentanoate, butyl myristate, propyl myristate, cetyl myristate, ethyl hexyl cocoate, isopropyl palmitate, 2-ethylhexyl palmitate, butyl stearate, hexadecyl stearate, isopropyl stearate, octyl stearate, isocetyl stearate, propyl or isostearyl isostearate, decyl or dodecyl oleate, hexyl laurate and propylene glycol dicaprylate, esters derived from lanolic acid, such as isopropyl lanolate and isocetyl lanolate, fatty acid monoglycerides, diglycerides and triglycerides such as glycerol triheptanoate, capryl-caprylic triglyceride, diisopropyl or ethylhexyl adipate, neopentylglycol diheptanoate, diisopropyl or diethylhexyl sebacate, myristyl or lauryl lactate, diethylhexyl maleate, alkyl benzoates, isoparaffins, polyalphaolefins, polyolefins such as polyisobutene, synthetic isoalkanes such as isohexadecane and isododecane, perfluorinated oils and silicone oils. Among the latter, those which may be mentioned more particularly are dimethylpolysiloxanes, methylphenylpolysiloxanes, silicones modified by amines, silicones modified by fatty acids, silicones modified by alcohols, silicones modified by alcohols and fatty acids, silicones modified by polyether groups, epoxy-modified silicones, silicones modified by fluoro groups, cyclic silicones and silicones modified by alkyl groups.

This oil can also be selected from fatty acids, fatty alcohols, waxes of natural or synthetic origin and, more generally, any fats of vegetable, animal or synthetic origin.

The primary emulsion with an oily outer phase also comprises from 0.1 to 25%, preferably 1 to 25%, and most preferably 1 to 5% by weight of an emulsifier.

Emulsifiers which may be mentioned in particular among those capable of being used within the framework of the present invention are lipoamino acids and their salts; lipopeptides and their salts; non-ionic and anionic silicone-based emulsifiers; sorbitan esters, for example the product called MONTANE® 80; mannitan and xylitan esters; polyglycerol esters, for example the products marketed under the names ISOLAN® G134 and DIISOSTEARYL PLUROL®; ethoxylated castor oil and ethoxylated hydrogenated castor oil, for example the product called SIMULSOL® 989; glycerol stearate; polyglycol or polyglycerol polyhydroxystearates, for example the products called HYPERMER®, ARLACEL® P135, DEHYMULS® PGPH and DECAGLYN®; polyethylene glycol/alkyl glycol copolymers, for example a PEG-45/dodecyl glycol copolymer such as the product marketed under the name ELFACOS ST 9®; ethoxylated sorbitan esters, for example the products marketed under the names MONTANOXO®, ARLACEL® 581 and ARLACEL® 582; protein acylates with a low degree of ethoxylation (from 1 to 3 EO groups); ethoxylated beeswax, for example the product called APIFIL®; cationic emulsifiers such as amine oxides, quaternium 82 and the surfactants described in patent application WO 96/00719, principally those whose fatty chain contains at least 16 carbon atoms; sucrose esters; ethoxylated or non-ethoxylated methylglucoside esters; ethoxylated fatty acids; ethoxylated fatty alcohols; anionic emulsifiers such as decylphosphate or cetearylsulfate; aluminum polyoxystearate, for example the product marketed under the name MANALOX®; magnesium stearate; and aluminum stearate.

Advantageously, the emulsifier used will be of the type described in patent applications FR-A-2668080, FR-A-2734496, FR-A-2762317, FR-A-2784904 and FR-A-2 790 977, particularly xylose derivatives.

It may also be advantageous to use an emulsifier based on alkylpolyglycosides and fatty diols and comprising especially:

5 to 95 parts by weight of a mixture of alkylpolyglycosides consisting of the reaction products of a saccharide and a dimeric diol having 36 carbon atoms; and 95 to 5 parts by weight of a dimeric diol having 36 carbon atoms.

The preferred emulsifiers defined as above comprise:

5 to 60 parts by weight of the above-mentioned mixture of alkylpolyglycosides; and 95 to 40 parts by weight of a dimeric diol having 36 carbon atoms.

The mixture of alkylpolyglycosides consisting of the reaction products of a saccharide and a dimeric diol having 36 carbon atoms actually consists of a mixture in any proportions of hydroxyalkylpolyglycosides (products resulting from the acetalization of one of the two hydroxyl groups of the dimeric diol) and polyglycosylalkylpolyglycosides (products resulting from the acetalization of both the hydroxyl groups of the dimeric diol).

These alkylpolyglycosides can be represented respectively by formulae I and II below:

in which:

G is a saccharide residue;

R is a disubstituted group derived from the dimeric alcohol originating from the hydrogenation of dimeric acid; and n, m and p are the mean degrees of polymerization of each of the saccharide residues.

The product known under the name "dimeric acid" is a dibasic acid having 36 carbon atoms in which the major compound can be represented by the formula

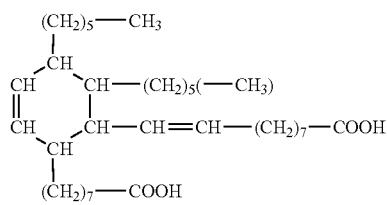

The saccharide residue present in the above-mentioned alkylpolyglycosides can be a glucose or dextrose, fructose, galactose, mannose, ribose or xylose residue, preferably a glucose or xylose residue.

It should also be noted that each unit of the polyoside part of the above-mentioned alkylpolyglycosides can be in the α or β anomeric form and the saccharide residue can be of the furanoside or pyranoside type.

The mean degree of polymerization of each saccharide residue is generally between 1.05 and 2.5 and preferably between 1.1 and 2.

The term "alkylpolyglycoside" used within the framework of the present patent application therefore arbitrarily denotes an alkylmonooside (degree of polymerization equal to 1) or an alkylpolyglycoside (degree of polymerization greater than 1).

The dimeric diol used to prepare the above emulsifier is a diol originating from the hydrogenation of dimeric acid.

It is marketed especially by COGNIS under the name SPEZIOL® C 36/2.

Because of its origin, this compound can contain minor proportions of impurities. Such impurities can be present in amounts ranging up to 30% by weight, based on the total weight of diol.

Consequently, the emulsifiers based on alkylpolyglycosides and fatty diols can comprise such impurities, or the reaction products of these impurities with a saccharide, in corresponding minor proportions.

The emulsifiers based on alkylpolyglycosides and fatty diols which can be used within the framework of the present invention can be prepared by simply mixing their constituents in desired predetermined proportions.

On the industrial scale they will preferably be prepared by one of the two methods conventionally used for the synthesis of alkylpolyglycosides, for example by reacting the dimeric diol and a saccharide having an anomeric OH, such as glucose or dextrose, in an acid medium.

If appropriate, this synthesis may be completed with operations involving neutralization, filtration, distillation or partial extraction of the excess fatty diol, or decolorization.

It may also be advantageous to use an emulsifier based on an alkylpolyxyloside of the formula

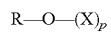

in which:

p is a decimal number between 1 and 5,

X is the xylose residue, and

R is a branched alkyl radical:

in which m is an integer between 6 and 18, n is an integer between 4 and 18 and the sum n+m is greater than or equal to 14;

or a composition consisting of a mixture of at least two compounds as defined above; or a composition comprising:

more than 0% by weight and less than 100% by weight, preferably from 1% to 60% by weight, of a compound defined above or a mixture of such compounds, and more than 0% by weight and less than 100% by weight, preferably from 40% to 99% by weight, of a compound of the formula ROH or a mixture of such compounds, in which R is as defined above.

In this embodiment, compositions containing an alkylpolyxyloside R—O—(X)$_p$ and the corresponding alcohol ROH, in the proportions indicated above, are particularly preferred.

The oligomeric structure (X)$_p$ can exhibit any form of isomerism, i.e. optical isomerism, geometrical isomerism or position isomerism; it can also represent a mixture of isomers.

In the formula R—O—(X)$_p$, the group R—O— is bonded to X by the anomeric carbon of the saccharide residue to form an acetal group.

p, which represents the mean degree of polymerization of the saccharide, is more particularly between 1 and 2.5 and very particularly between 1 and 2.0.

The compound of the formula R—O—(X)$_p$ can be prepared by reacting a compound of the formula

with an excess of a fatty alcohol of the formula ROH and then removing the unreacted fatty alcohol.

In the process as defined above, the formation reaction of the alcohol ROH is carried out in the presence of strong acid catalysts, for example mineral acids such as sulfuric acid, hypophosphorous acid or a mixture of these acids.

In one variant of the process as defined above, the xylose of the formula HO—X is reacted with an alcohol of the formula R$_1$—OH, in which R$_1$ contains from 1 to 4 carbon atoms, and more particularly with butanol, to give the acetal of the formula R$_1$O—(X)$_p$, which is then subjected to a transacetalization with an excess of an alcohol of the formula ROH, with distillation of the alcohol of the formula R$_1$OH formed, followed by removal of the unreacted alcohol of the formula ROH.

In this process and its variant as described above, the unreacted alcohol of the formula ROH is removed by methods known to those skilled in the art, for example by distillation, thin film distillation, molecular distillation or solvent extraction.

The primary emulsion with an oily outer phase can also comprise a stabilizer.

Stabilizers which may be mentioned among those capable of being used within the framework of the present invention are hydrogenated castor oil; vegetable or animal waxes, for example beeswax, candellila and carnauba wax; stearic acid; silicas including hydrophobic silicas; polymers such as the products marketed under the name KRATON®; mineral waxes such as ozokerite; clays such as hectorite or bentonite; and hydrophobic modified starches, for example the product marketed under the name DRY FLOW PC®; hydrophobic methacrylates and polymethyl methacrylates such as the products marketed under the name MICROPEARL MHB® or POLYTRAP®.

The primary emulsion with an oily outer phase also advantageously comprises one or more mineral salts, for example magnesium chloride, magnesium sulfate or sodium chloride, in an amount ranging from 0.05% to 5% by weight, preferably between 0.1% and 5%, and most preferably between 0.1% and 2% by weight.

The primary emulsions with an oily outer phase according to the present invention can be prepared by simply dispersing the aqueous phase in the oily phase at a temperature of between 15° C. and 90° C., in the presence of the emulsifier(s) and optionally the stabilizer(s).

In a manner known per se, these emulsions can also comprise one or more compounds selected from humectants, for example glycerol, glycols, or the sodium salt of 2-pyrrolidone 5-carboxylic acid; preservatives, for example the products known under the name SEPICIDE®; colorants; perfumes; cosmetic active ingredients; mineral or organic sunscreen agents; mineral fillers such as iron oxides, titanium oxides and talcum; synthetic fillers such as nylons and crosslinked or non-crosslinked polymethyl methacrylates; silicone elastomers; sericites; and plant extracts.

These compounds may be introduced into the aqueous phase or into the oily phase, depending on their affinity for these phases, either during the above-mentioned dispersion phase or, as regards the temperature-sensitive compounds, subsequently during the cooling phase in the case where the dispersion is prepared under the action of heat.

As specified above, the primary emulsion with an oily outer phase can be added to the aqueous gel or vice-versa. The aqueous gel is obtained by gelling an aqueous phase with a polymer. Said polymer is advantageously present in an amount of between 0.02 and 10% by weight, preferably of between 0.4 and 8% by weight, of the aqueous gel.

Polymers which may be mentioned in particular among those capable of being used within the framework of the present invention are homopolymers or copolymers of acrylic acid, acrylic acid derivatives, acrylamide, acrylamidomethanepropanesulfonic acid, a vinylic monomer and trimethylaminoethyl acrylate chloride, for example the products marketed under the names CARBOPOL®, PEMULEN®, SIMULGEL® A, SIMULGEL® NS, SIMULGEL® EPG, SIMULGEL® EG, LUVIGEL® EM, SALCARE® SC91, SALCARE® SC92, SALCARE® SC95, SALCARE® SC96, FLOCARE® ET100, HISPAGEL®, SEPIGEL® 305, SEPIGEL® 501, SEPIGEL® 502, FLOCARE® ET58 and STABWLEZE® 06; hydrocolloids of vegetable or biosynthetic origin, for example xanthan gum, karaya gum, carrageenates and alginates; silicates; cellulose and its derivatives; and starch and its hydrophilic derivatives.

The aqueous gel has a viscosity greater than 2000 cPs, preferably greater than 20,000 cPs, measured on a BROOKFIELD LV viscometer at 6 rpm.

The topical composition according to the invention has a fresh, pleasant and non-sticky texture.

The composition of the invention can thus advantageously be used in a cosmetic, pharmaceutical or veterinary preparation. The composition of the invention can also be used in a detergent preparation.

According to a particularly favoured aspect, the present invention relates to a new sunscreen emulsion consisting of an oily outer phase and two inner aqueous phases, and to a process for the preparation of said emulsion.

Sunscreen emulsions must fulfil a certain number of criteria:

they must have a sufficient photoprotective effect. This factor is measured by determining the ability of a sunscreen emulsion to reduce erythema caused by ultra-violet irradiation;

it is preferable that they possess water resistance properties, i.e. once spread on skin, they conserve as far as possible their photoprotective function after the user of the emulsion goes swimming;

in order for the user to be comfortable, it is desirable that the topical sunscreen compositions have practical and sensory qualities. In particular, they should be easy to spread, and should not give have a greasy feel nor be sticky.

A large number of sunscreen compositions have been developed based on "oil-in-water" emulsions. When enough of the oily phase is used, this type of emulsion has the advantage of facilitating the dissolution of sunscreen filter substances, most of whom are lipophilic or lipodispersible organic compounds, and also enables good sensory properties to be achieved viz. a soft feel and easy spreading.

The water resistance of "oil-in-water" emulsions is however weak. It is consequently often necessary to use additives which "structure" or "rigidify" the aqueous phase, such as poly(vinylpyrrolidone), polyacrylates, polyacrylamides or silicone oils, which increase the water-repelling properties of the film.

The addition of such additives is often deleterious to the sought-after sensory properties.

One avenue that has therefore been explored is to formulate "water-in-oil" emulsions. However, such emulsions have the disadvantage of being difficult to spread and, as far as their sensory properties are concerned, are judged to have a greasy feel.

According to this preferred aspect of the invention, the use of certain types of "water-in-oil" emulsion enables all the criteria mentioned above to be simultaneously met.

It is in particular possible to combine a high degree of photoprotection with enhanced water resistance, whilst maintaining ease of spreading and acceptable sensory properties (non-greasy feel, non-sticky).

This aspect of the invention is thus in particular directed to sunscreen emulsions consisting of an external oily phase and two internal aqueous phases one of which is a gel, the oily phase comprising an emulsifying system, where one or more sunscreen filters are incorporated into the oily phase and/or into the gelified aqueous phase.

As regards the oils to be used in the preparation of sunscreen emulsions according to the present invention, any of the oils listed above for preparation of emulsions according to the present invention may be used, but the preferred oils for this aspect of the invention are chosen from among the group consisting of: fatty acid esters such as isodecyl neopentanoate, butyl myristate, propyl myristate, cetyl myristate, isopropyl palmitate, 2-ethylhexyl palmitate, butyl stearate, hexadecyl stearate, isopropyl stearate, octyl stearate, isocetyl stearate, dodecyl oleate, hexyl laurate, propylene glycol dicaprylate, lanolic acid esters such as isopropyl lanolate and isocetyl lanolate, monoglycerides, diglycerides and triglycerides of fatty acids such as glycerol triheptanoate, caprylic capric triglyceride, C12-C15 alkyl benzoate, diisopropyl adipate, ethylhexyl cocoate, ethylhexyl adipate, diisopropyl or diethylhexyl sebacate, myristyl or lauryl lactate, diethylhexyl maleate.

As regards the emulsifying system to be used in the preparation of sunscreen emulsions according to the present invention, any of the emulsifiers listed above for preparation of emulsions according to the present invention may be used, but the preferred emulsifying systems for this aspect of the invention comprise at least one emulsifier chosen from among the group consisting of: alkylpolyglycosides, mixtures comprising a mixture of alkylpolyglycosides and fatty alcohols, polyglycerol, polyglycol or polyol esters, which may optionally be alkoxylated, such as polyglycol or polyglycerol polyhydroxystearates (optionally alkoxylated), and polyethyleneglycol/alkylglycol copolymers.

A particularly preferred embodiment of the emulsifying system to be used in the preparation of sunscreen emulsions according to the present invention consists in a combination of, on the one hand, a polyglycol polyhydroxystearate, a polyol polyhydroxystearate (optionally alkoxylated), a polyglycerol ester or a polyethyleneglycol/alkylglycol copolymer, and on the other hand, an alkylpolyglycoside or a composition contain both alkylpolyglycosides and fatty alcohols.

The emulsifying system to be used in the preparation of sunscreen emulsions according to the present invention may consist in an emulsifer as detailed above and a co-emulsifier.

The sunscreen emulsions according to the present invention may contain up to 10% by weight of such a co-emulsifier.

Among the co-emulsifiers that can be used within the framework of the present invention are lipoamino acids and their salts; lipopeptides and their salts; sorbitan and mannitan esters, ethoxylated hydrogenated castor oil, glycerol stearate, cationic emulsifiers such as amine oxides, quatemium 82, sucrose esters, ethoxylated methylglycoside esters (optionally ethoxylated), ethoxylated fatty acids, ethoxylated fatty alcohols, and anionic emulsifiers such as decylphosphate or cetearylsulfate.

The sunscreen emulsions according to the invention comprise a photoprotective system containing one or more sunscreen filters, which can be incorporated into the oily and/or aqueous phases of the emulsions.

In general, the sunscreen filter substance(s) is/are incorporated into the oily phase, into the gelified aqueous phase or, advantageously, into each of these phases. It is nevertheless possible in certain circumstances that the "non-gelified" aqueous phase of the emulsion contain one or more hydrosoluble or hydrodispersible filter substances.

When the gelified aqueous phase comprises one or more sunscreen filters, the latter is/are in general dispersed directly into the gelified aqueous phase if the filter(s) is/are liquid. If the filter(s) is/are solid, they are generally dispersed beforehand in a solvent such as ethanol or in another, liquid sunscreen filter that solubilizes them, before incorporation into the aqueous gel.

The sunscreen filters can be organic or inorganic in nature, and it is possible to combine organic and inorganic filters in the same sunscreen emulsion.

Among organic filters, the following substances can be used: members of the family of benzoic acid derivatives such as para-aminobenzoic acid (PABA), and in particular monoglycerol esters of PABA, ethyl esters of N,N-propoxy PABA, ethyl esters of N,N-diethoxy PABA, ethyl esters of N,N-dimethyl PABA, methyl esters of N,N-dimethyl PABA, butyl esters of N,N-dimethyl PABA; the family of anthranilic acid derivatives such as homomenthyl-N-acetyl-anthranilate; the family of salicylic acid derivatives such as amyl salicylate, homomenthyl salicylate, ethylhexyl salicylate, phenyl salicylate, benzyl salicylate, p-isopropanolphenyl salicylate; the family of cinnamic acid derivatives such as ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyle cinnamate (p-methoxy 2-ethylhexyl cinnamate), p-methoxy 2-ethoxyethyl cinnamate, p-methoxycyclohexyl cinnamate, ethyl-α-cyano-β-phenyl cinnamate, 2-ethylhexyl-αcyano-βphényl cinnamate, diparamethoxy mono-2-ethylhexanoyl glyceryle cinnamate; the family of benzophenone derivatives such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-pheynylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,1-camphor, 3-(benzylidene)-d,1-camphre, benzalkonium methosulfate camphre; urocanic acid, ethyl urocanate; the family of sulfonic acid derivatives such as 2-phenylbenzimidazole-5-sulfonic acid and its salts; the family of triazine derivatives such as hydroxyphenyl triazine, ethylhexyloxyhydroxyphenyl-4-methoxyphenyltriazine, 2,4,6-trianilino-(p-carbo-2'-ethylhexyl-1'-oxy)-1,3,5-triazine, benzoic acid 4,4-((6-(((1,1-dimethylethyl)amino)carbonyl)phenyl) amino)-1,3,5-triazine-2,4-diyl-diimino)bis-(2-ethylhexyl) ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl)benzotriazole;

dibenzazine; dianisoylmethane, 4-methoxy-4"-t-butylbenzoylmethane; 5-(3,3-dimethyl-2-norbornylidene)-3-pentan-2-one; the family of diphenylacrylate derivatives such as 2-ethylhexyl-2-cyano-3,3-diphenyl-2-propenoate, ethyl-2-cyano-3,3-diphenyl-2-propenoate; the polysiloxane family such as benzylidene siloxane malonate.

Among the class of inorganic filters, also called "mineral screens", one may note titanium oxides, zinc oxides, cerium oxides, zirconium oxides, yellow, red and black iron oxides, and chromium oxides. These mineral screens can be micronized or not, and may or may not have been subjected to surface treatments and may optionally be present in the form of aqueous or oily pre-dispersions.

As regards the polymers used for the preparation of the gelified aqueous phase of the sunscreen emulsions according to the present invention, any of the polymers listed above for preparation of emulsions according to the present invention may be used, but preferred polymers for this aspect of the invention comprise one or more polymers chosen among the group consisting of homopolymers and copolymers containing acrylamidomethanepropanesulfonic acid and its salts, acrylic acid and its salts and derivatives, acrylamide and its derivatives.

In an advantageous manner, sunscreen emulsions according to the present invention may further comprise cosmetic active ingredients such as water-soluble vitamins and vitamin derivatives, lipophilic vitamins and vitamin derivatives, oligosaccharides, proteins, peptides, amino acids, N-acylated derivatives of amino acids, peptides and proteins, plant extracts, and extracts from marine algae.

Sunscreen emulsions according to the present invention, consisting of an oily external phase and two internal aqueous phases, one of which is a gel, contain between 1 and 40% by weight of sunscreen filters with respect to the weight of the emulsion, preferably between 2 and 35%, and more preferably between 5% and 25% by weight of the emulsion.

The invention will be illustrated by the Examples which follow.

EXAMPLE 1

A composition is prepared according to the following procedure:

a) An oily phase "A" and an aqueous phase "B" are heated to 80° C.;

b) a primary emulsion "C" with an oily outer phase is formed by mixing the aqueous phase "B" into the oily phase "A", sufficient stirring being maintained until the mixture has completely cooled;

c) an aqueous gel "D" with a viscosity of 80,000 cPs, measured on a BROOKFIELD LV viscometer at 6 rpm, is formed by dispersing the polymer in the aqueous phase; and d) the emulsion is incorporated into the gel (or the gel into the emulsion, cf. Table 1), in a gel/emulsion weight ratio of 70/30, by simply stirring by hand.

| Primary emulsion "C" | | Aqueous gel "D" | |
|---|---|---|---|
| MONTANOV ® WO18 | 8% | Carbomer | 0.4% |
| Polyisobutene | 19% | Water qsp | 100% |
| A Paraffin oil | 21% | SEPICIDE ® HB | 0.2% |
| ELFACOS ® ST9 | 2% | Triethanolamine | 0.5% |
| SEPICIDE ® HB | 1% | | |
| Water qsp | 100% | | |
| B Glycerol | 5% | | |
| MgSO$_4$.7H$_2$O | 0.7% | | |

The composition obtained has an oily outer phase, as confirmed by measurement of the conductivity (<5 μS·cm), and also comprises two aqueous inner phases, one of which is a gel.

The presence of these two aqueous phases is demonstrated as follows: The primary emulsion is prepared using an aqueous phase "B" comprising a hydrophilic colorant, for example the pink colorant marketed by WACKHERR under the name W4506. When the final composition is observed under the microscope, the two disperse phases are clearly identified, the one having a pink coloration and the other being colorless.

TABLE 1

| Procedure | Result and properties |
|---|---|
| Introduction of the primary emulsion "C" into the aqueous gel "D"* | composition with oily outer phase 2 aqueous inner phases observed under the microscope oil content: 12% by weight |
| Introduction of the aqueous gel "D" into the primary emulsion "C"* | composition with oily outer phase 2 aqueous inner phases observed under the microscope oil content: 12% by weight |

*with anchor-type stirring for 10 min at 300 rpm

COMPARATIVE EXAMPLE 1 a) Composition obtained according to Example 1

| MONTANOV ® WO18 | 2.4% |
|---|---|
| Polyisobutene | 5.7% |
| Paraffin oil | 6.3% |
| ELFACOS ® ST9 | 0.6% |
| SEPICIDE ® HB | 0.44% |
| Water qsp | 100% |
| Carbomer | 0.28% |
| Triethanolamine | 0.35% |
| MgSO$_4$.7H$_2$O | 0.21% |
| Glycerol | 1.5% | b) By way of comparison, a "water-in-oil" emulsion is separately prepared in conventional manner from the following oily and aqueous phases:

| Oily phase | | Aqueous phase | |
|---|---|---|---|
| MONTANOV ® WO18 | 8% | MgSO$_4$.7H$_2$O | 0.7% |
| Polyisobutene | 5.7% | Glycerol | 1.5% |
| Paraffin oil | 6.3% | Water qsp | 100% |
| ELFACOS ® ST9 | 2% | | |
| SEPICIDE ® HB | 0.44% | | |

NB: It will be noted that, although the concentrations of emulsifier and stabilizer have been increased (relative to the emulsion of a)) to give an emulsion of sufficient stability, the concentrations of oils are identical.

An emulsion with an oily outer phase is indeed obtained (conductivity<5 μS·cm).

The composition according to the invention and the "comparative" emulsion were subjected to a sensory evaluation by a jury of 20 persons. The results are shown in Table 2.

TABLE 2

| Score out of 10 (mean of the jury) | Invention | Comparative |
|---|---|---|
| Spreadability (positive criterion) | 8 | 2 |
| Sensation of freshness (positive criterion) | 8.5 | 3 |
| Residue (negative criterion) | 2 | 7 |
| Stickiness (negative criterion) | 1 | 8 |

EXAMPLE 2

The procedure of Example 1 is repeated using the following primary emulsion and aqueous gel (of viscosity 70,000 cPs, Brookfield LV, 6 rpm) in a weight ratio of 50/50:

| Primary emulsion | | Aqueous gel | |
|---|---|---|---|
| Dimethicone copolyol | 2% | SIMULGEL ® EG | 2% |
| Cyclomethicone DC ® 345 (Dow Corning) | 23% | Water | 98% |
| LANOL ® 99 (isononyl isononanoate) | 5% | | |
| SEPICIDE ® HB | 0.3% | | |
| Water qsp | 100% | | |
| Glycerol | 5% | | |
| Sodium chloride | 2% | | |
| SEPICIDE ® CI | 0.2% | | |

The composition obtained has an oily outer phase (conductivity<5 µS·cm) and comprises two aqueous inner phases, one of which is a gel. The oil content is 15% by weight.

EXAMPLE 3

First of all, an emulsifier of the alkylpolyglycoside type is prepared as follows:

792.8 g of $C_{36}$ dimeric alcohol (marketed by COGNIS under the name SPEZIOL $C_{36/2}$) are introduced into a two-liter glass reactor equipped with a high-efficiency mechanical stirrer, a jacket heating system, a condenser and a temperature probe.

The dimeric alcohol is heated to 90° C. and 112.0 g of xylose are dispersed in the reaction medium and then homogenized at 90°/95° C. for 15 minutes.

1.90 g of 98% sulfuric acid and 1.31 g of 50% hypophosphorous acid are added and the reaction mixture is kept at 95° C. for 4 hours under a partial vacuum while nitrogen is being bubbled through.

After cooling to 80° C., a solution of sodium borohydride in sodium hydroxide solution is added in order to neutralize the mixture until the pH of a 5% solution of the reaction medium is about 7.1.

The resulting product is in the form of a clear viscous liquid with a free alcohol content of 50% by weight. This product is called "APG1" hereafter.

The procedure of Example 1 is repeated using the following primary emulsion and aqueous gel in a weight ratio of 50/50:

| Primary emulsion | | Aqueous gel | |
|---|---|---|---|
| APG1 | 8% | SIMULGEL ® 600 | 2% |
| ELFACOS ® ST9 | 2% | Water | 98% |
| Paraffin oil | 30% | | |
| LANOL ® 1688 (cetearyl ethylhexanoate) | 10% | | |
| Water qsp | 100% | | |
| Glycerol | 5% | | |
| MgSO$_4$.7H$_2$O | 0.7% | | |

The composition obtained has an oily outer phase (conductivity<5 µS·cm) and comprises two aqueous inner phases, one of which is a gel. The oil content is 20% by weight.

EXAMPLE 4

The procedure of Example 1 is repeated using the following primary emulsion and aqueous gel in a gel/emulsion weight ratio of 80/20:

| Primary emulsion | | Aqueous gel | |
|---|---|---|---|
| Isostearyl APX* | 10% | SIMULGEL ® EG | 1.5% |
| Squalane | 40% | Water | 98.5% |
| Water qsp | 100% | | |
| Glycerol | 5% | | |
| MgSO$_4$.7H$_2$O | 0.7% | | |

*prepared by the procedure described in Example 1 of patent application FR-A-2 790 977, the glucose being replaced with xylose The composition obtained has an oily outer phase (conductivity<5 µS·cm) and comprises two aqueous inner phases, one of which is a gel. The oil content is 8%.

EXAMPLES 5-8 AND COMPARATIVE EXAMPLES 2-6

General Procedure for Preparing Sunscreen Emulsions

The preparation of sunscreen emulsions according to the present invention can be carried out according to the following method:

a) an oily phase "A" is prepared, comprising the oil or oils, the lipophilic emulsifying system, and optionally a co-emulsifier. These ingredients are mixed and the resulting oily phase is heated to 50° C. One or more sunscreen filter substances are then added to this heated oily phase. This phase may also optionally contain lipodispersible mineral sunscreens;

b) at the same time as the oily phase is being prepared according to step (a), an aqueous phase "B" is prepared, containing water, optionally one or more mineral salts and optionally glycerine as a humectant. This phase is also heated to 50° C.; this phase can also possibly contain water-soluble sunscreen filters or water-dispersible mineral sunscreens;

c) a primary emulsion "C" with an oily outer phase is made by mixing the aqueous phase "B" into the oily phase "A" whilst continuing to stir sufficiently, until the mixture has completely cooled;

d) separately, an aqueous gel "D" is prepared by dispersing one or more thickening polymers in water, which may also contain preservatives and perfumes;

e) in certain cases, one or more sunscreen filter substances may be dispersed beforehand so as to make a liquid phase and then the resulting liquid phase is added to the aqueous gel "D". If the sunscreen filter(s) is/are solid(s), ethanol as a solvent, or a separate, liquid sunscreen filter substance, may be used to solubilize the the solid sunscreen(s) before they are added;

f) the emulsion is incorporated into the gel (or the gel into the emulsion) with gentle stirring.

According to the type of sunscreen emulsion to be prepared, some of steps (a) to (f) listed above may either be modified or not carried out at all. Depending on the physiochemical nature of the sunscreen filter substances to be incorporated, it is also possible to modify the temperatures to which the oily phase "A" and aqueous phase "B" are heated before being mixed together.

General Methods for Assessing the Properties of Sunscreen Emulsions

Determination of SPF (Sun Protection Factor)

The sun protection index (PI) or sun protection factor (SPF) is defined as being equal to the quotient of the minimal erythemal dose obtained using a photoprotective product (MEDp) divided by the minimal erythemal dose where no product is used (MEDnp), according to the following equation:

$$SPF = MEDp/MEDnp$$

The MED, expressed in millijoules, corresponds to the smallest amount of light energy needed to give rise to a visible and even erythema with defined borders.

Under normal test conditions for SPF evaluation, volunteers invited to the laboratory read an information sheet which reminds them of the conditions of the test, before signing a form of consent.

To begin, colorimetric measurements are taken of the sites to be irradiated using a machine such as the MINOLTA Chromameter®. In effect, the skin type must be identified, since the test results varies considerably as a result of the subject's skin color. Human skin types are treated here as being divided into six categories, type I corresponding to the whitest skin encountered, which burns after exposure to sunlight and does not tan at all. Type VI corresponds to the darkest of all skin hues, people showing this phototype (generally of African origin) having a skin which (almost) never burns.

For these tests it is preferred to use here volunteers of phototypes II and III, these being the most representative of subjects likely to suffer a major increase in erythema following exposure to UV radiation.

Afterwards 2 mg of the sunscreen product is applied per $cm^2$ of the zone to be irradiated. Reference products from COLIPA (European Cosmetic Toiletry and Perfumery Association) are always tested at the same time, which enables the validity of the experiment to be monitored.

Fifteen minutes after the products are applied to the volunteer's ski, the selected zones are irradiated using a xenon lamp in a geometric progression of factor 1.25, according to the presumed protection index of the tested product and the reference product. The xenon lamp can for example be a short arc lamp marketed under the name IDEM 3000® Arquantiel, which irradiates over a spectrum going from 290 to 400 nm. Infra-red radiation is filtered using a filter of the UG11 type (1 mm), and IR elimination is also achieved using a water filter and ventilation. The irradiated surface must have an area of at least 1 $cm^2$. The power of the emitting source is about 1000 W.

A typical system has six orifices with separate shutters. Successive opening of each of the orifices at fixed moments in time by the operator of the machine enables a geometric progression of the UV dose received by the volunteer to be achieved (geometric progression of 1.25).

At a point in time lying between 16 and 24 hours after irradiation, a readout is taken of both the Minimal Erythemal Dose without protection (MEDnp) and the MED with protection (MEDp), both for the reference product and the tested product.

Determination of Water Resistance of Sunscreen Compositions

The persistence of a sunscreen product is studied by UV irradiation after a test of water resistance. This test is carried out by giving two baths at a temperature of 30±2° C. to volunteers for a duration of 20 minutes, with a pause of ten minutes between the two baths (referred to as a "standardized bath"). The first bath is taken 15 minutes after the application of the sunscreen composition to be tested.

The percentage of persistence is calculated according to the following formula:

$$\% \text{ persistence} = SPFwr/SPF \times 100$$

where

SPF=Protection index when dry $SPF_{wr}$=Protection index determined after water resistance test It is generally considered that products showing less than 50% persistence cannot be classified as water resistant. A percentage persistence lying between 50% and 80% corresponds to an acceptable level of water resistance for a sunscreen product. By contrast, sunscreen compositions having a percentage persistence equal to or greater than 80% (and which thus show "high water resistance") are particularly sought after in the framework of the present invention.

Sensory Evaluation

Sensory evaluation of tested products was carried out by a panel of experts (typically a jury of 20 people), who give marks on a scale of 1 to 10 for the following criteria:

| | | |
|---|---|---|
| Ease of spreading: | very easy = 10 | very difficult = 0 |
| Greasy feeling: | very greasy = 10 | no greasy feeling = 0 |
| Sticky effect: | very sticky = 10 | no sticky effect = 0 |

EXAMPLES OF PREPARATION OF SUNSCREEN EMULSIONS

EXAMPLE 5 AND COMPARATIVE EXAMPLES 2 TO 4

A sunscreen emulsion having the composition indicated in example 1 was prepared according to the general method described above. The photoprotective index and the percentage water resistance were determined according to the procedures described in the preceding sections. Following this, sensory evaluation was carried out via a panel of experts.

At the same time, comparative examples were performed in conditions giving rise to a "oil-in-water" gel-cream (obtained without an emulsifying system), or to emulsions consisting in an outer oily phase and a single internal aqueous phase.

The comparative results from the experiments are presented in Table 3.

TABLE 3

| Nature of product obtained | Comparative Example 2 Gel cream O/W | Comparative Example 3 Emulsion W/O | Comparative Example 4 Emulsion W/O | Example 5 Emulsion W/O with two aqueous phases |
|---|---|---|---|---|
| Emulsifying system | | | | |
| PEG30 dipolyhydroxystearate | — | 0.6% | 0.6% | 0.6% |
| Fluidanov ® 20X (3) | — | 2.4% | 2.4% | 2.4% |
| Oily phase | | | | |
| Caprylic capric triglyceride | 12% | 12% | 12% | 12% |
| Microcristalline wax | — | — | 5% | — |
| Filter system | | | | |
| Titanium oxide (1) | 3% | 3% | 3% | 3% |
| Zinc oxide (2) | 3% | 3% | 3% | 3% |
| Ethylhexyl salicylate | 3.5% | 3.5% | 3.5% | 3.5% |
| Ethylhexylmethoxycinnamate | 5.25% | 5.25% | 5.25% | 5.25% |
| Polymer | | | | |
| SIMULGEL ® EG | 3% | — | — | 2.1% |
| Other additives | | | | |
| $MgSO_4$ | — | 0.7% | 0.7% | 0.021% |
| Glycerol | — | 1.5% | 1.5% | 1.5% |
| preservatives | qs | qs | qs | qs |
| Water qsp 100% | | | | |
| Stability | Granular | Unstable | Stable | Stable |
| Photoprotective index | — | — | 18 +/− 3 | 18 +/− 3 |
| % water resistance | — | — | 65% +/− 10 | 68% +/− 10 |
| Sensory evaluation | | | | |
| Ease of spreading | — | — | 2 | 9 |
| Greasy feeling | | | 8 | 1 |
| Sticky effect | | | 8 | 0 |

(1) MT100T SUNSMART
(2) Z COTE HP1 TAYCA
(3) alkylpolyxyloside based on 2-octyldodecanol, manufactured according to patent application EP-A-1142901

It is observed that only the emulsion according to the present invention (Example 5) combines at the same time water resistance properties with a good ease of spreading, a non-greasy feel and an absence of stickiness, with a photoprotection index similar to that of comparative example 4, which represents a known technique in the art for the preparation of water-in-oil emulsions stabilized by the presence of microcristalline wax and which does not involve the use of the process according to the present invention.

EXAMPLE 6

A sunscreen emulsion is prepared this time with the following components:

| | | |
|---|---|---|
| 1. | FLUIDANOV ® 20X | 2% |
| 2. | PEG30 dipolyhydroxystearate | 0.5% |
| 3. | $C_{12}$–$C_{15}$ alkyl benzoate | 5% |
| 4. | Water | 5% |
| 5. | Magnesium sulfate heptahydrate | 0.02% |
| 6. | Glycerol | 1.5% |
| 7. | Titanium oxide UV TITAN ® M160 | 10% |
| 8. | SIMULGEL ® NS | 2% |
| 9. | Water | qsp 100% |
| 10. | Ethanol | 15% |

-continued

| | | |
|---|---|---|
| 11. | Ethylhexyl methoxycinnamate | 7.5% |
| 12. | Benzophenone-3 | 2.5% |
| 13. | Ethylhexyl salicylate | 5% |
| 14. | Additives: preservatives, perfume | qs |

Ingredients 1 to 3 are mixed and heated to 50° C. Ingredient 7 is added and then a primary emulsion is formed with the aqueous phase constituted by 4+5+6 (also heated to 50° C.). A gel is then formed from 8+9 and, separately, 11+12+13 are solublized in 10. This phase is then added to the gel. Thereafter the primary emulsion is also added to the gel.

At the end of this procedure, a sunscreen emulsion PI35 is obtained, which possesses a water resistance value of 90%. This emulsion procures a light feeling, is not sticky and is very easy to spread. It is easy to prepare and only contains 5% of oil; the organic filters are dissolved in a hydroalcoholic gel and the mineral fillers are dispersed in the primary W/O emulsion.

Sensory evaluation produced the following marks:

Ease of spreading: 9

Greasy feel: 1

Sticky effect: 2

EXAMPLE 7 AND COMPARATIVE EXAMPLE 5

The aim here was to compare emulsions according to the present invention, prepared as described in Example 5, with a composition, which is generally similar but does not contain a lipophilic surfactant. This reference system, usually called a gel-cream, is very widely used in the cosmetic care sector because it meets the requisite sensory criteria. However, this system is little used in sunscreen applications on account of its weak water resistance. The reformulation of gel-creams using the method according to the present invention, whilst also using a lipophilic surfactant system, enables the weak points of the system to be corrected, and enables formulations to be prepared, which combine photoprotective performance, water resistance and pleasant sensory properties.

TABLE 4

| Example<br>Nature of product obtained | Comparative<br>Example 5<br>Gel cream<br>O/W | Example 7<br>W/O emulsion with<br>2 aqueous phases |
|---|---|---|
| Emulsifying system | | |
| PEG30 dipolyhydroxystearate | — | 0.4% |
| Fluidanov ® 20X | — | 1.6% |
| Oily Phase | | |
| Diisopropyl adipate | 12% | 12% |
| Filter system | | |
| Ethylhexyl salicylate | 5% | 5% |
| Ethylhexyl methoxycinnamate | 5% | 5% |
| Ethylhexyldimethyl p-aminobenzoate | 8% | 8% |
| Butylmethoxydibenzoylmethane | 2% | 2% |
| Polymer | | |
| SIMULGEL ® NS | 3% | 3% |
| Other additives | | |
| $MgSO_4$ | — | 0.02% |
| Glycerol | 1.5% | 1.5% |
| preservatives | qs | qs |
| Water qsp 100% | | |
| Stability | stable | stable |
| Photoprotection index | 15 +/− 3 | 25 +/− 3 |
| % water resistance | 18% +/− 10 | 61% +/− 10 |
| Sensory evaluation | | |
| Ease of spreading | 10 | 9 |
| Greasy feel | 2 | 3 |
| Sticky effect | 0 | 0 |

EXAMPLE 8 AND COMPARATIVE EXAMPLE 6

The experimental method of Example 7 and Comparative Example 5 is repeated, but this time using a different oily phase and a mineral sunscreen filter.

TABLE 5

| Example<br>Nature of product obtained | Comparative<br>Example 6<br>O/W Gel<br>cream | Example 8<br>W/O Emulsion with<br>two aqueous phases |
|---|---|---|
| Emulsifying system | | |
| PEG30 dipolyhydroxystearate | — | 0.6% |
| Fluidanov ® 20X | — | 2.4% |
| Oily phase | | |
| Caprylic capric triglyceride | 12% | 12% |
| Filter system | | |
| Titanium dioxide UV TITAN ® m160 | 10% | 10% |
| Polymer | | |
| SIMULGEL ® EG | 2.1% | 2.1% |
| Other additives | | |
| $MgSO_4$ | — | 0.02% |
| Glycerol | 1.5% | 1.5% |
| Preservatives | qs | qs |
| Water qsp 100% | | |
| Stability | Granular | Stable |
| Photoprotection index | — | 20 +/− 3 |
| % water resistance | — | 52% +/− 10 |
| Sensory evaluation | | |
| Ease of spreading | — | 7 |
| Greasy feeling | | 3 |
| Sticky effect | | 1 |

The method according to the present invention enables a mineral sunscreen filter to be incorporated with a gelification step of the aqueous phase, leading to a water-in-oil emulsion, whereas stabilization is impossible after the aqueous phase is gelified in the oil-in-water situation, without a surfactant system as in the present invention.

Overall Conclusion

The method of preparing sunscreen emulsions according to the present invention provides the following advantages:

Photoprotecting formulas showing excellent water resistance, comparable to traditional W/O emulsions known in the art, can be obtained;

The emulsions obtained have very promising sensory properties similar to those of gel-cream formulations. The latter formulations are little used in the solar protection filed as they are not very compatible with mineral sunscreens, do not provide efficient photoprotection, and are not water-resistant.

What is claimed is:

1. A topical sunscreen composition, comprising a three-phase emulsion consisting essentially of at least one sunscreen filter, an emulsifier, one oily outer phase and two aqueous inner phases, one of said inner phases being a gel having a viscosity greater than 2000 cPs, as measured on a Brookfield LV at 6 rpm, and said at least one sunscreen filter being contained in at least one of said phases,
    wherein the gel phase comprises a polymer selected from the group consisting of homopolymers and copolymers of acrylic acid, acrylic acid derivatives, acrylamide, and acrylamidomethanepropanesulfonic acid, and
    wherein the oily outer phase comprises an oil in an amount of at least 2% and at most 20% by weight of the topical sunscreen composition.

2. The composition according to claim 1, wherein the oily outer phase comprises an oil in an amount of 5 to 20% by weight of the topical sunscreen composition.

3. A sunscreen composition according to claim 1, wherein the emulsifier is selected from the group consisting of alkylpolyglycosides, alkylpolyglycosides derived from fatty alcohols and the corresponding fatty alcohols, polyglycerol esters, polyglycol esters, polyol esters, alkoxylated polyglycerol esters, alkoxylated polyglycol esters, alkoxylated polyol esters and polyethyleneglycol/alkylglycol copolymers and mixtures thereof.

4. A sunscreen composition according to claim 3, wherein the emulsifier is a combination of a first emulisifier which is a polyglycol polyhydroxystearate, a polyol polyhydroxystearate or alkoxylated polyol polyhydroxystearate, a polyglycerol ester or a polyethyleneglycol/alkylglycol copolymer, and a second emulsifier which is an alkylpolyglycoside or a composition containing both alkylpolyglycosides and fatty alcohols.

5. A sunscreen composition according to claim 1, wherein the sunscreen filter comprises 2% to 40% by weight of the topical sunscreen composition.

6. A sunscreen composition according to claim 5, wherein the sunscreen filter comprises 5% to 20% by weight of the topical sunscreen composition.

7. A sunscreen composition according to claim 1, wherein the gel phase comprises a polymer in an amount of 0.02% to 10% by weight of the gel phase.

8. A sunscreen composition according to claim 7, wherein the polymer is present in the gel phase in an amount of 0.4 to 8% by weight.

9. A sunscreen composition according to claim 1, which further comprises at least one mineral filler.

10. A process for the manufacture of a sunscreen composition comprising a three-phase emulsion consisting essentially of at least one sunscreen filter, an emulsifier, one oily outer phase and two aqueous inner phases, one of said inner phases being a gel having a viscosity greater than 2000 cPs, as measured on a Brookfield LV at 6 rpm, and said at least one sunscreen filter being contained in at least one of said phases, wherein the gel phase comprises a polymer selected from the group consisting of homopolymers and copolymers of acrylic acid, acrylic acid derivatives, acrylamide, and acrylamidomethanepropanesulfonic acid, and wherein the oily outer phase comprises an oil in an amount of at least 2% and at most 20% by weight of the sunscreen composition, comprising the step of mixing a primary water-in-oil emulsion with an aqueous gel.

11. The process according to claim 10, wherein 5 to 80% by weight of the primary emulsion is mixed with 20 to 95% by weight of the aqueous gel.

12. The process according to claim 11, wherein 5 to 80% by weight of the primary emulsion is mixed with 40 to 90% by weight of the aqueous gel.

13. The process according to claim 10, wherein the primary emulsion is introduced into the aqueous gel.

14. The process according to claim 10, wherein the aqueous gel is introduced into the primary emulsion.

15. The process according to claim 10, wherein the aqueous gel is obtained by gelling an aqueous phase with a polymer.

16. The process according to claim 15, wherein said polymer is present in an amount of between 0.02 and 10% by weight of the aqueous gel.

17. The process according to claim 10, wherein said viscosity is greater than 20000 cPs.

18. The process according claim 10, wherein the primary emulsion comprises from 5 to 90% by weight of oil.

19. The process according to claim 10, wherein the primary emulsion comprises from 1 to 25% by weight of the emulsifier.

* * * * *